United States Patent
Nakagawa et al.

(10) Patent No.: US 9,541,452 B2
(45) Date of Patent: Jan. 10, 2017

(54) CALIBRATION CURVE FORMATION METHOD, IMPURITY CONCENTRATION MEASUREMENT METHOD, AND SEMICONDUCTOR WAFER MANUFACTURING METHOD

(71) Applicant: GlobalWafers Japan Co., Ltd., Niigata (JP)

(72) Inventors: Satoko Nakagawa, Tokyo (JP); Kazuhiko Kashima, Tokyo (JP)

(73) Assignee: GlobalWafers Japan Co., Ltd. (JP)

( * ) Notice: Subject to any disclaimer, the term of this patent is extended or adjusted under 35 U.S.C. 154(b) by 87 days.

(21) Appl. No.: 14/719,771

(22) Filed: May 22, 2015

(65) Prior Publication Data

US 2015/0338276 A1    Nov. 26, 2015

(30) Foreign Application Priority Data

May 23, 2014 (JP) ................................ 2014-107545

(51) Int. Cl.
*H01L 21/66* (2006.01)
*G01N 21/64* (2006.01)
(Continued)

(52) U.S. Cl.
CPC .......... *G01J 3/4406* (2013.01); *G01N 21/6489* (2013.01); *G01N 21/9501* (2013.01); *H01J 37/3171* (2013.01); *H01L 21/265* (2013.01); *H01L 22/10* (2013.01); *G01J 2003/2873* (2013.01); *G01N 21/274* (2013.01)

(58) Field of Classification Search
CPC .......... G01J 2003/2873; G01N 21/274; G01N 21/6489; H01L 22/10
See application file for complete search history.

(56) References Cited

U.S. PATENT DOCUMENTS 5,841,532 A    11/1998  Yoshida et al.
6,217,651 B1 *  4/2001  Kashino .................. C23C 16/52
                                                                     117/82
(Continued)

FOREIGN PATENT DOCUMENTS

GB      2306640 A       5/1997
JP   2013-152977 A      8/2013

OTHER PUBLICATIONS

Extended European Search Report dated Nov. 5, 2015 regarding Application No. 15168715.9 (10 pages).
(Continued)

*Primary Examiner* — Raj R Gupta
(74) *Attorney, Agent, or Firm* — Harness, Dickey & Pierce, P.L.C.

(57) ABSTRACT

According to an embodiment, a method of forming a calibration curve is provided. The method includes ion-implanting different doses of an impurity into a plurality of first samples, measuring an intensity of photoluminescence deriving from the impurity by a photoluminescence spectroscopy for the first samples and a second sample made of the same semiconductor. Based on the amount of implanted impurity, the intensity of the photoluminescence, and a concentration of the impurity contained in the second sample measured by a method other than the photoluminescence spectroscopy, a calibration curve is formed.

13 Claims, 1 Drawing Sheet

(51) Int. Cl.
  *C30B 29/06* (2006.01)
  *G01J 3/44* (2006.01)
  *H01J 37/317* (2006.01)
  *H01L 21/265* (2006.01)
  *G01N 21/95* (2006.01)
  *G01J 3/28* (2006.01)
  *G01N 21/27* (2006.01)

(56) References Cited

U.S. PATENT DOCUMENTS

2004/0235231 A1* 11/2004 Narendar ............... C01B 31/36 438/202
2015/0284873 A1* 10/2015 Kreszowski ............ C01B 33/02 117/38

OTHER PUBLICATIONS

Satoko Nakagawa, et al. "Quantitative Analysis of Carbon Impurity Concentration in Silicon Epitaxial Layers by Luminescence Activation Using Carbon Ion Implantation and Electron Irradiation." Physica Status Solidi. C: Current Topics in Solid State Physics, vol. 11, No. 11-12, (Sep. 12, 2014) (pp. 1597-1600)(10 Pages).

Satoko Nakagawa-Toyota, et al. "Characterization of Light Element Impurities in Ultrathin Silicon-on-Insulator Layers by Luminescence Activation Using Electron Irradiation." Japanese Journal of Applied Physics, vol. 48, No. 3 (Mar. 1, 2009) (pp. 031201.1-031201.4) (5 pages).

S. Nakagawa, et al. "Photoluminescence Evaluation of Light Element Impurities in Ultrathin SOI Wafers by Luminescence Activation Using Electron Irradiation." Material Science and Engineering B 134 (2006) (pp. 172-175) (4 pages).

M. Nakamura, et al. "Photoluminescence Measurement of Carbon in Silicon Crystals Irradiated with High Energy Electrons." Journal of Electrochemical Society, vol. 141, No. 12 (Dec. 1994) (pp. 3576-3580) (5 pages).

S. Nakagawa, et al. "Quantitative Analysis of Low-Concentration Carbon in Silicon Wafers by Luminescence Activation Using Electron Irradiation." The Forum on the Science and Technology of Silicon Materials 2010, Tsushima-Naka, Japan (JSPS), (pp. 326-331) (6 pages).

* cited by examiner

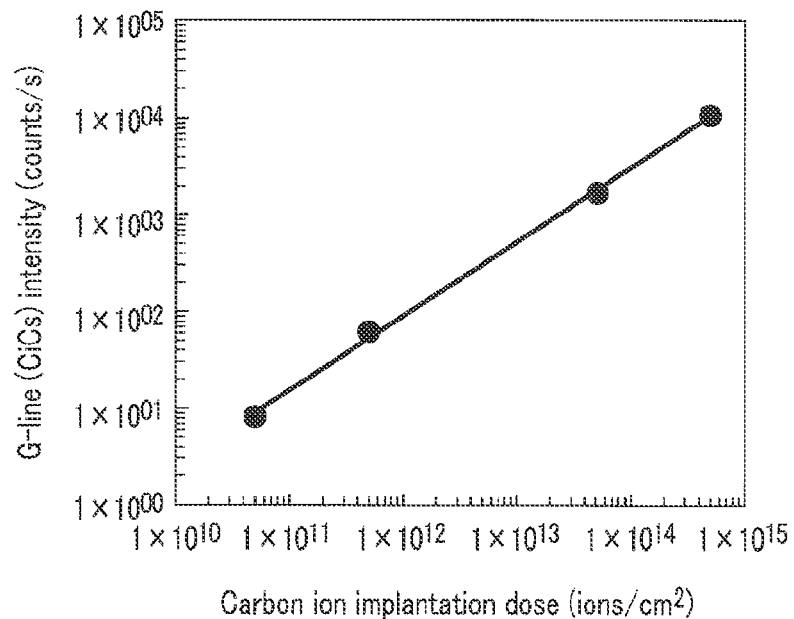
F I G. 1
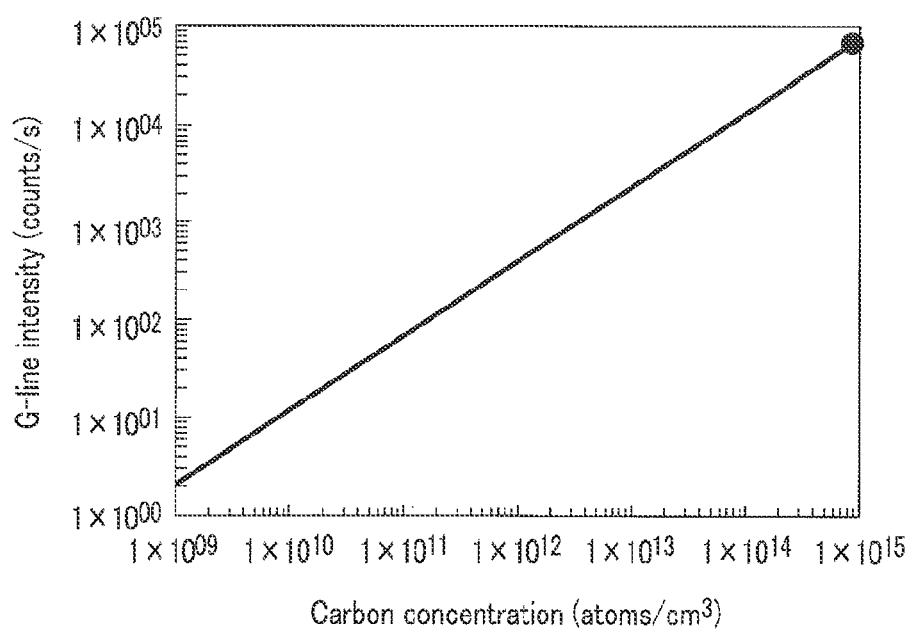
F I G. 2

CALIBRATION CURVE FORMATION METHOD, IMPURITY CONCENTRATION MEASUREMENT METHOD, AND SEMICONDUCTOR WAFER MANUFACTURING METHOD

CROSS-REFERENCE TO RELATED APPLICATIONS

This application is based upon and claims the benefit of priority from Japanese Patent Application No. 2014-107545, filed May 23, 2014, the entire contents of which are incorporated herein by reference.

FIELD

The present invention relates to a calibration curve which is used to measure the concentration of an impurity in a semiconductor.

BACKGROUND

Impurities contained in a semiconductor wafer have a large influence on the performance of a semiconductor device. For this reason, it is desirable to know and control an impurity concentration during manufacture of a semiconductor wafer. For example, carbon in a semiconductor wafer lowers the withstand voltage of a power device. Accordingly, demands have risen for reducing a carbon concentration in, e.g., a single-crystal silicon layer formed on an epitaxial silicon wafer by an epitaxial growth method (referred to as an epitaxial silicon layer, hereinafter).

A silicon wafer having a single-layer structure obtained by slicing an ingot normally contains carbon at a relatively high concentration ($1\times10^{15}$ atoms/cm$^3$ or more), and this carbon concentration can be measured by a known method. Also, since this silicon wafer has the single-layer structure, the carbon concentration can be measured by a transmission method such as Fourier-transform infrared spectroscopy (FT-IR).

On the other hand, in many epitaxial silicon wafers, an epitaxial silicon layer has a carbon concentration of less than $1\times10^{14}$ atoms/cm$^3$. This concentration is lower than the lower detection limit of an apparatus which measures carbon concentration by known methods such as secondary ion mass spectrometry (referred to as SIMS, hereinafter). Also, since the epitaxial wafer has a multilayer structure, when the transmission method is used, layers other than the epitaxial silicon layer are also measured, and so transmission methods such as infrared absorption spectrometry cannot be applied.

Jpn. Pat. Appln. KOKAI Publication No. 2013-152977 describes a method of measuring the concentration of an impurity in a semiconductor wafer by a photoluminescence spectroscopy (referred to as a PL method, hereinafter). In this method, a calibration curve indicating the relationship between the concentration of an impurity in a semiconductor wafer and the intensity of photoluminescence (referred to as PL, hereinafter) deriving from the impurity is formed in advance. Then, the PL intensity of a semiconductor wafer having an unknown impurity concentration is measured, and the impurity concentration is obtained by referring the measurement result to the calibration curve. Note that the calibration curve is formed by using a semiconductor wafer having a known impurity concentration.

As described above, in many epitaxial silicon wafers, the carbon concentration of an epitaxial silicon layer is lower than the lower detection limit of a measurement apparatus. Therefore, when the method described in Jpn. Pat. Appln. KOKAI Publication No. 2013-152977 is applied to the measurement of the carbon concentration in the epitaxial layer, it becomes difficult to form a calibration curve having a small error.

SUMMARY

It is an object of the present invention to make it possible to accurately measure the concentration of an impurity in a semiconductor.

According to a first aspect, a formation method of forming a calibration curve is provided. The method comprises ion-implanting different doses of an impurity into a plurality of first samples made of the same semiconductor, and measuring by a photoluminescence spectroscopy, for each of the plurality of first samples into which the impurity is ion-implanted, an intensity of photoluminescence deriving from the impurity. A relationship between the amount of the implanted impurity and the intensity of the photoluminescence is obtained from the measurement. The method also comprises measuring by the photoluminescence spectroscopy, for a second sample made of the same semiconductor as that of the plurality of first samples, an intensity of photoluminescence deriving from the impurity contained in the second sample. The measurement for the second sample is performed under the same conditions as those for the measurement for each of the plurality of first samples. The method further comprises forming a calibration curve representing a relationship between the concentration of the impurity and the intensity of the photoluminescence deriving from the impurity. The calibration curve is formed based on the relationship, the intensity of the photoluminescence obtained for the second sample, and a concentration of the impurity contained in the second sample, which is measured by a method other than the photoluminescence spectroscopy.

According to a second aspect, a measurement method of measuring an impurity concentration in a semiconductor is provided. The measurement method uses the calibration curve formed by the formation method according to the first aspect. The measurement method comprises measuring by a photoluminescence spectroscopy, for a first measurement target made of a semiconductor manufactured under the same conditions as those for the first sample, an intensity of photoluminescence deriving from an impurity contained in the first measurement target. The method further comprises obtaining a concentration of the impurity contained in the first measurement target by referring the intensity of the photoluminescence deriving from the impurity contained in the first measurement target to the calibration curve.

According to a third aspect, a manufacturing method of manufacturing a semiconductor wafer is provided. The manufacturing method uses the measurement method according the second aspect. The manufacturing method comprises manufacturing a plurality of wafers made of a semiconductor, extracting a portion of the plurality of wafers, using at least a portion of the extracted wafers as a first measurement target, and measuring a concentration of an impurity contained in the extracted wafer by using the measurement method. The method also comprises comparing the concentration of the impurity contained in the extracted wafer with a predetermined upper limit. In the method, if the concentration of the impurity contained in the extracted wafer exceeds the upper limit, it may be determined that the rest of the plurality of wafers may also have a high impurity concentration, or it may be determined that the manufacturing of the plurality of wafers is out of specification.

BRIEF DESCRIPTION OF DRAWINGS

FIG. 1 is a graph showing an example of the relationship between the implantation dose of an impurity and the PL intensity; and FIG. 2 is a graph showing an example of a calibration curve representing the relationship between the impurity concentration and PL intensity.

MODES FOR CARRYING OUT THE INVENTION

An embodiment of the present invention will be explained below.

First, a calibration curve formation method according to the embodiment of the present invention will be explained.

This calibration curve formation method includes the following procedures.

First, different doses of an impurity are ion-implanted into a plurality of first samples made of the same semiconductor.

The first sample is, e.g., a semiconductor wafer. The first sample is made of, e.g., silicon.

The first sample can have either a single-layer structure or multilayer structure. The first sample having the multilayer structure is, e.g., an epitaxial wafer obtained by forming one or more single-crystal semiconductor layers on a semiconductor substrate by epitaxial growth (referred to as epitaxial layers, hereinafter). The first sample may also be a fragment obtained by cutting a semiconductor wafer.

The impurity implanted into the first sample is the same type of impurity whose concentration is to be measured using the calibration curve. This impurity is, e.g., carbon.

As an example, the first sample is an epitaxial silicon wafer obtained by forming an epitaxial silicon layer on a silicon single-layer wafer. In this example, the impurity is carbon.

A sufficient number of first samples is two or more. The accuracy of the calibration curve increases as the number of first samples different in impurity implantation dose increases.

When the number of first samples is three or more, if the dose of impurity implanted into a given first sample differs from that of another first sample, two or more first samples can have the same impurity implantation dose. The accuracy of the calibration curve can be increased by using the average value of data obtained for the first samples having the same amount of implanted impurity implantation.

Desirably, the difference between the maximum and minimum values of the dose of impurity implanted into the first sample is sufficiently large. When the first sample is an epitaxial silicon wafer and the impurity is carbon, the dose of impurity implanted into the first sample is preferably determined such that the ratio of the maximum value to the minimum value of the doses of implantation is 10 or more.

When the above-described ion implantation is performed, the crystal structure of the semiconductor is damaged. Therefore, a crystallinity recovery process (crystallinity recovery annealing), for example, is performed on the first sample into which the impurity is implanted.

When the first sample is made of silicon or includes an epitaxial silicon layer, the annealing temperature is preferably 700° C. to 1,200° C., and more preferably, 900° C. to 1,100° C. Note that when the purpose is to recover the crystallinity of silicon, the lower limit of the annealing temperature is generally considered to be about 900° C. However, even at 700° C., the crystallinity recovers to some extent.

Also, in this case, the annealing time is preferably adjusted in accordance with the thickness of the sample. For example, when the sample thickness is about 500 μm, the annealing time is preferably 10 min or more. When the thickness of a sample is small and the sample sufficiently reaches the annealing temperature within a short time, the crystallinity sufficiently recovers within a shorter time.

The crystallinity recovery annealing is preferably performed under an inert gas atmosphere such as nitrogen or argon. Such inert gases have no reactivity, and therefore, even if such inert gases are contained in crystal, they have no influence on, e.g., the formation of a calibration curve.

A recrystallization process may also be performed on the impurity-implanted first sample, instead of the crystallinity recovery process. When this recrystallization process is performed, the distribution of implanted impurity becomes uniform in the recrystallized region.

In the recrystallization process, e.g., an amorphousization process and rapid thermal processing (RTP) are performed in this order on the impurity-implanted first sample.

In the amorphousization process, a noble gas such as argon is ion-implanted into the first sample. In this process, a material having no influence on the evaluation of a target impurity can be implanted instead of the noble gas.

The rapid thermal processing is a process of rapidly heating the first sample under an inert gas atmosphere such as nitrogen, thereby melting and crystallizing the semiconductor of the first sample. In this rapid thermal processing, for example, the first sample is heated to 1,100° C. for 30 sec. When the rapid thermal processing is performed following the amorphousization process, the impurity diffuses and uniformly distributes in the first sample.

Next, the intensity of photoluminescence (PL) deriving from the impurity in the semiconductor is measured by the PL method for each first sample. Thus, the relationship between the amount of ion-implanted impurity and the PL intensity obtained by the PL measurement is obtained.

In the same manner as in a normal method of measuring the amount or concentration of impurity in a semiconductor by the PL method, a luminescence-activation process is performed on the semiconductor, then the semiconductor is irradiated with excitation light, and the PL intensity is measured, in this PL measurement. As an example, a case in which the first sample is an epitaxial silicon wafer and the impurity is carbon will be explained below.

First, a luminescence-activation process for the impurity is performed. More specifically, the wafer is irradiated with an electron beam.

In the wafer before it is irradiated with an electron beam, the carbon impurity exists as substitutional carbon. That is, carbon atoms substitute silicon atoms in the crystal lattice, so no photoluminescence occurs even when irradiated with excitation light. When irradiated with an electron beam, carbon in the wafer is rendered luminescence-active by the following mechanism, and PL measurement is enabled.

When the wafer is irradiated with an electron beam, a portion of silicon atoms occupying the lattice points of the silicon crystal become interstitial atoms, and a vacancy is formed at the same time. Thus, a primary defect is introduced to the silicon crystal. This introduction of the primary defect to the silicon crystal is represented by the following formula:

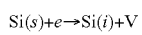

$$Si(s) + e \rightarrow Si(i) + V$$

wherein V represents the vacancy, Si(s) represents an Si atom that is positioned in the lattice point of the silicon crystal, Si(i) represents an Si atom that is positioned between the lattice points in the silicon crystal, and e represents an electron.

When the first defect is introduced to the silicon crystal, substitutional carbon C(s) replaces interstitial silicon Si(i) and becomes interstitial C(i) as represented by the following formula:

$$Si(i)+C(s)\rightarrow Si(s)+C(i)$$

In addition, interstitial carbon C(i) forms a complex defect Ci-Cs together with carbon C(s) occupying the lattice point as represented by the following formula:

$$C(i)+C(s)\rightarrow Ci\text{-}Cs$$

Alternatively, interstitial carbon C(i) forms a complex defect Ci-Oi together with interstitial oxygen O(i) contained in the crystal as presented by the following formula:

$$C(i)+O(i)\rightarrow Ci\text{-}Oi$$

The complex defects Ci-Cs and Ci-Oi thus formed exhibit photoluminescence when irradiated with excitation light.

The irradiation dose of the electron beam is preferably $1\times10^{13}$ electrons/cm$^2$ to $1\times10^{17}$ electrons/cm$^2$. The highest carbon impurity concentration in the carbon-implanted epitaxial silicon layer that can be expected is $5\times10^{14}$ atoms/cm$^3$. When the dose of electron beam irradiation is set at $1\times10^{13}$ electrons/cm$^2$ or more, luminescence-activation can sufficiently activate carbon of this concentration.

On the other hand, if the dose exceeds $1\times10^{17}$ electrons/cm$^2$, irradiation damage to the epitaxial wafer becomes great. Great irradiation damage is unfavorable because the number of non-radiative centers in the epitaxial layer increases. The non-radiative center has a defect level but does not exhibit photoluminescence, therefore the PL intensity decreases if the number of non-radiative centers increases.

A particle beam other than an electron beam can be used in the luminescence-activation of an impurity such as carbon. The impurity may be irradiated with, for example, high-energy particles such as protons or various ions. However, the particle sizes of protons or various ions are larger than that of an electron. Therefore, when the wafer is irradiated with these energy particles, not only is the vacancy (V) simply introduced, but the generation of a secondary defect such as a vacancy cluster increases, as compared to irradiation with an electron beam. Accordingly, when a silicon wafer containing a carbon impurity is irradiated with protons, photoluminescence other than that deriving from the carbon impurity increases. Examples of such photoluminescence, which are not found for electron beam irradiation, are photoluminescence deriving from interstitial silicon, photoluminescence deriving from crystal strain, and photoluminescence deriving from irradiation damage. In addition, the number of non-radiative centers increases. As a consequence, it becomes difficult to obtain an accurate correlation between the impurity concentration and PL intensity.

When performing PL measurement for a carbon impurity in a silicon semiconductor, therefore, it is possible to accurately capture low-carbon-concentration fluctuations by suppressing photoluminescence irrelevant to carbon concentration evaluation and decreasing the number of non-radiative centers. Accordingly, an electron beam is the most suitable irradiation species for use in luminescence-activation. Electron beam irradiation is also favorable in that the irradiation damage is small.

Immediately after the impurity luminescence-activation process, the PL intensity may decrease depending on the conditions of luminescence-activation. This is because a large number of irradiation defects which recover at room temperature may have generated immediately after the luminescence-activation process. In this case, the photoluminescence intensity can be increased by, e.g., leaving the sample to stand at room temperature for a long time or annealing the sample at a low temperature. Note that annealing must be performed under conditions by which carbon-related photoluminescence does not recover.

When the first sample having undergone the luminescence-activation process is irradiated with excitation light, photoluminescence deriving from the impurity is obtained. For example, when the first sample is a silicon wafer and the impurity is carbon, photoluminescence (G-line) having photon energy of 0.97 eV is obtained from a complex defect Ci-Cs. Also, a silicon wafer normally contains a slight amount of oxygen, and photoluminescence (C-line) having photon energy of 0.79 eV is obtained from a complex defect Ci-Oi.

Photoluminescence measured by PL measurement is not necessary photoluminescence deriving from an impurity. For example, in a silicon semiconductor, electron-hole pairs are generated when silicon is photoexcited, and free-exciton luminescence (FE luminescence) is observed. Note that an aggregate of a plurality of FEs is called an electron-hole droplet (EHD), and photoluminescence deriving from the EHD is called EHD luminescence.

FE luminescence is photoluminescence intrinsic to a semiconductor in a crystalline state. Therefore, the intensity of the FE luminescence is an index indicating the crystallinity. Accordingly, increase or decrease in intensity of the FE luminescence indicates a change in crystallinity of a semiconductor. This makes it possible to use the FE luminescence intensity as, e.g., an index for determining whether the crystallinity has sufficiently recovered by crystallinity recovery annealing after ion implantation.

Furthermore, bound-exciton luminescence (BE luminescence) may be observed for general impurities. A bound exciton (BE) is an exciton bound in an impurity or in a defect in a semiconductor. Photon energy released by recombination of BEs is BE luminescence. Since the spectral line of BE luminescence is very sharp, an impurity contributing to BE luminescence is readily discerned. Examples of impurities contributing to BE luminescence are general dopants such as boron (B), phosphorous (P), aluminum (Al), and arsenide (As). Note that the dopant is added to adjust the resistivity of a semiconductor.

Generally, the penetration depth of excitation light into a sample changes in accordance with the wavelength of the excitation light. Therefore, an excitation light wavelength may be selected in accordance with an evaluation region in order to adjust the penetration depth of the excitation light. For example, when measuring G-line of an epitaxial layer of an epitaxial silicon wafer, if the penetration depth of excitation light is too large, the excitation light may penetrate not only the epitaxial layer but also a silicon substrate below the epitaxial layer. In this case, carbon in the silicon substrate is also photoexcited, so the measured G-line intensity does not accurately reflect the carbon concentration in the epitaxial layer. As an example of appropriate selection of an excitation light wavelength, it is favorable to use excitation light having a wavelength of 650 nm or less for an epitaxial layer having a thickness of 10 μm or more.

Note that when excitation light is selected such that the above-described problem with respect to the penetration depth does not arise, the penetration depth of the excitation light may be equal to, smaller than, or larger than the implantation depth of an impurity. Also, when excitation light is selected such that the above-described problem with respect to the penetration depth does not arise, the implantation depth of an impurity can change from one first sample to another. However, excitation light is preferably selected such that the sum of the penetration depth of the excitation light and the diffusion length of an excited carrier exceeds the implantation depth of an impurity.

The PL intensity is preferably measured as follows. For example, the first sample is immersed in a cryogenic liquid such as liquid helium and held at a constant temperature. A sample may generate heat when irradiated with an excitation laser during PL measurement. If the temperature of a semiconductor sample fluctuates, various photoluminescence balances such as FE luminescence and dopant-derived BE luminescence change. By immersing the sample in a cryogenic liquid, it is possible to avoid heat generation by the sample, and make the temperatures of all samples uniform. This makes stable evaluation possible.

The PL intensity can be controlled by the dose of impurity implanted into the first sample. The dose of impurity implanted into the first sample is preferably controlled within a range in which PL measurement can be performed on each sample under the same conditions. For example, PL measurement can be performed without changing the measurement conditions when the ratio of the maximum value of the implantation dose of an impurity to the minimum value is set to $10^7$ or less. As an example, when the first sample is an epitaxial silicon wafer and the impurity is carbon, the PL intensity may increase too much if the implantation dose of carbon exceeds $1\times10^{16}$ ions/cm$^2$. By contrast, if the implantation dose of carbon is less than $1\times10^9$ ions/cm$^2$, the PL intensity may become lower than the detection limit. Note that if the carbon implantation dose is too small, the G-line intensity may not change from that when no carbon is implanted. Accordingly, the carbon implantation dose is set equal to or larger than a minimum amount with which a change in G-line intensity can be observed relative to a sample into which no carbon is implanted.

The PL intensity is influenced by the temperature of crystallinity recovery annealing after ion implantation. For example, when the first sample is an epitaxial silicon wafer and the impurity is carbon, the G-line intensity and C-line intensity change in accordance with the annealing temperature. G-line becomes dominant when neither ion implantation nor crystallinity recovery annealing is performed or when low-temperature annealing is performed, and C-line becomes dominant when high-temperature annealing is performed. Since it is desirable to measure the G-line intensity, high-temperature annealing, in which C-line becomes dominant, is unfavorable.

Note that when the dopant concentration is high, no photoluminescence (including photoluminescence other than BE luminescence) may be obtained due to the influence of Auger recombination. For example, the dopant concentration is preferably $1\times10^{18}$ atoms/cm$^3$ or less.

Next, the relationship between the amount of ion-implanted impurity and the PL intensity deriving from the impurity is obtained for the first sample. For example, when the first sample is an epitaxial silicon wafer and the impurity is carbon, a straight line is obtained by plotting the logarithm of the G-line intensity with respect to the logarithm of the ion implantation dose of carbon.

The reason that the slope of this log-log plot of the PL intensity with respect to the ion implantation dose of impurity depends on only the impurity concentration will be explained below.

In the above-described example, i.e., when the first sample is an epitaxial silicon wafer and the impurity is carbon, the log-log plot of the ion implantation dose of carbon and the G-line intensity has a linear relationship. When the G-line intensity is represented by $[G_{PL}]$, the ion implantation dose is represented by $[C_{imp}]$, a slope of the plot of the G-line intensity with respect to the ion implantation dose is represented by a, and an intercept of the log-log plot is represented by b, this relationship can be represented by the following equation:

$$[G_{PL}] = b \times [C_{imp}]^a$$

Since the carbon implantation dose is directly reflected on the G-line intensity in this equation, the total concentration of carbon cannot be obtained from this equation. Also, strictly speaking, carbon contributing to photoluminescence, i.e., the ratio of carbon rendered luminescence-active depends on various uncertainties, e.g., implantation damage during ion implantation, the recovery factor of crystallinity during crystallinity recovery annealing, and the ion implantation profile. Let us assume that these uncertainties are A, and that the ratio of carbon rendered luminescence-active depends on the carbon concentration. That is, let us assume that there is a relationship represented by the following equation:

$$[C_{imp}] = A \times [C_s]$$

Substituting this equation into the above-mentioned equation of the log-log plot of the ion implantation dose of carbon and the G-line intensity yields the following equation:

$$[G_{PL}] = b \times [AC_s]^a$$

This equation is rewritten as follows:

$$\log [G_{PL}] = \log b + a \log A + a \log [C_s]$$

$$\log [G_{PL}] = \log(bA^a) + a \log [C_s]$$

$$[G_{PL}] = bA^a \times [C_s]^a$$

Thus, the uncertainties A can be represented as a function independent of the slope a. Also, as shown in the above-mentioned equation, the uncertainties A are contained in a term corresponding to the intercept of the log-log plot. Accordingly, the slope of the log-log plot of the G-line intensity with respect to the ion implantation dose of carbon directly represents the slope of the log-log plot of the G-line intensity with respect to the carbon concentration in an epitaxial layer. That is, by obtaining the correlation between the carbon implantation dose and G-line intensity, the correlation between the carbon concentration in the epitaxial layer and the G-line intensity, i.e., the relative concentration of carbon with respect to the G-line intensity can be obtained.

The G-line intensity is used in the above-described example, i.e., in the case in which the first sample is an epitaxial silicon wafer and the impurity is carbon. However, the log-log plot may also be obtained by using a relative intensity, e.g., the ratio of the FE luminescence intensity to the G-line intensity, or the ratio of the EHD luminescence intensity to the G-line intensity, instead of the G-line intensity.

Also, in an example in which the first sample is a silicon wafer and the impurity is carbon, the balance between the C-line intensity and G-line intensity changes due to the oxygen concentration in the silicon semiconductor. Therefore, to accurately obtain the relationship between the G-line intensity and the ion implantation dose of impurity, the oxygen concentrations among each of the first samples are preferably equal. When the first sample is an epitaxial silicon wafer, the oxygen concentration is very low, i.e., much lower than $1\times10^{15}$ atoms/cm$^3$, and hence can be regarded as constant.

In addition, when the first sample is a silicon wafer and the impurity is carbon, the C-line intensity can also be used because C-line is photoluminescence deriving from a carbon-derived defect and oxygen-derived defect. However, a calibration curve representing the relationship between the carbon concentration and PL intensity can be formed with higher accuracy by measuring the G-line intensity which is influenced relatively little by oxygen.

Note that as described above, when the first sample is an epitaxial silicon wafer, the oxygen concentration is low, so the C-line intensity is low. To obtain an accurate calibration curve, therefore, it is preferable to measure the G-line intensity rather than the C-line intensity.

In addition to the above-described series of procedures from ion implantation to PL measurement performed for the plurality of first samples, the following series of procedures are performed for a second sample made of the same semiconductor as that of the first sample. The series of procedures for the second sample include the preparation of the second sample, the measurement of the concentration of an impurity contained in the second sample performed by the existing measurement method, and PL measurement for the impurity of the second sample. These procedures for the second sample can be performed before, after, or in parallel with the procedures for the first sample.

As the second sample, a sample made of the same semiconductor as that of the first sample is prepared. For example, when the first sample is an epitaxial silicon wafer, the second sample is an epitaxial silicon wafer or a fragment obtained by cutting the wafer. Also, the second sample is, for example, a sample in which during the crystal growth process, an impurity has been introduced at a high concentration, more specifically, at a concentration sufficiently detectable by a method other than the PL method. The method of increasing the concentration of an impurity introduced into the second sample can also be achieved, for example, when the second sample is a wafer having an epitaxial layer, by adjusting the growth conditions of the epitaxial layer. More specifically, the carbon contamination amount can be increased by changing the heating conditions of a susceptor, which is a carbon contamination source, in the manufacture of an epitaxial silicon wafer.

A measurement method other than the PL method, which measures the impurity concentration of the second sample, is, e.g., measurement by SIMS.

The PL measurement on the second sample is performed in the same manner as for the first sample. For example, the G-line intensity is measured when the first sample is an epitaxial silicon wafer and the impurity is carbon.

Finally, based on the relationship between the dose of impurity ion-implanted into the semiconductor, which is obtained for the first sample, the concentration of the impurity contained in the second sample and measured by a known method, and the PL intensity deriving from the impurity of the second sample, a calibration curve representing the relationship between the concentration of the impurity contained in the semiconductor and the intensity of photoluminescence resulting from the impurity is formed.

The relationship between the amount of ion-implanted impurity and the PL intensity, which is obtained for the first sample, indicates the relative concentration of the impurity with respect to the PL intensity deriving from the impurity in the semiconductor. This relationship directly represents the slope of the calibration curve. A plot line having such a slope is translated on the log-log plot of the PL intensity with respect to the impurity concentration, so as to pass a point corresponding to the concentration of the impurity contained in the second sample and determined by a method other than the PL method and the impurity-derived PL intensity of the second sample, i.e., a point indicating the absolute concentration of the impurity with respect to the impurity-derived PL intensity, to obtain a calibration curve indicating the relationship between the impurity concentration and PL intensity.

More specifically, when the first and second samples are epitaxial silicon wafers and the impurity is carbon, for example, it is possible to form a calibration curve which has the slope obtained from the amount of ion-implanted carbon and the G-line intensity for each of the first samples (the relative concentration of carbon with respect to the G-line intensity), and passes a plot point on the log-log plot of the wafer impurity concentration and G-line luminescence intensity corresponding to the carbon concentration and G-line intensity of the second sample (the absolute concentration of carbon with respect to the G-line intensity).

In the calibration curve formation method explained above, the first and second samples are not limited to epitaxial silicon wafers, and the impurity is not limited to carbon.

Next, a method of measuring the impurity concentration in the semiconductor by using this calibration curve will be explained.

First, a measurement target is prepared. This measurement target is, for example, a semiconductor wafer manufactured by the same method and same conditions as those for the first sample, or a fragment obtained by cutting the wafer. In this case, the measurement target has the same composition and same structure as those of the first sample, aside from unavoidable fluctuations in composition and structure. Note that the above-described impurity implantation is not normally performed on this measurement target.

Then, the intensity of PL deriving from the impurity is measured by the PL method for the measurement target. For example, when the first and second samples are epitaxial silicon wafers and the impurity is carbon, the G-line intensity of the measurement target is measured. In this PL measurement, the conditions such as the wavelength of excitation light are the same as those of the PL measurement of the first and second samples.

Finally, the impurity concentration is obtained by referring the measured PL intensity to the calibration curve. For example, when the first and second samples are epitaxial silicon wafers and the impurity is carbon, the impurity concentration is obtained by referring to the calibration curve to look up the impurity concentration on the calibration curve corresponding to the G-line intensity obtained by the PL measurement. This measurement method does not require complicated concentration conversion.

The impurity concentration measurement method has been explained by taking the case in which the measurement target is an epitaxial silicon wafer containing a carbon impurity as an example. Note however, that the measurement target is not limited to an epitaxial silicon wafer, and the impurity is not limited to carbon.

A semiconductor wafer manufacturing method according to the embodiment of the present invention will be explained below. This manufacturing method is an application of the above-described measurement method.

Generally, a plurality of semiconductor wafers is manufactured from one semiconductor ingot. For example, when the first and second samples are epitaxial silicon wafers, a plurality of epitaxial wafers are manufactured from this ingot. A portion of the plurality of epitaxial wafers is extracted, and samples as impurity measurement targets are obtained from the extracted wafers.

The number of wafers to be extracted may be either one or plural. The sample obtained from the extracted wafer can be either an epitaxial wafer or a specimen obtained by cutting the wafer. Note that the impurity concentrations in the head and tail of an ingot are generally different, so the number of wafers to be extracted to obtain samples is preferably plural when the semiconductor wafer is not an epitaxial wafer.

Then, the PL intensity of the sample as a measurement target is measured, and the impurity concentration is obtained by referring this PL intensity to the calibration curve. For example, when manufacturing an epitaxial silicon wafer which may contain a carbon impurity, the G-line intensity of the sample as a measurement target is measured, and the carbon concentration is obtained by referring this G-line intensity to the calibration curve.

Subsequently, the obtained impurity concentration is compared with the upper limit preset for a semiconductor wafer as a product. This upper limit is set, for example, based on the correlation between the performance of the semiconductor wafer and the impurity concentration and the reference performance value required of the wafer product. When the semiconductor wafer is a silicon wafer, for example, the performance of the semiconductor wafer are device characteristics pertaining to the ON voltage such as a collector-emitter saturation voltage value or the carrier lifetime.

If the result of the comparison of the impurity concentration to this upper limit indicates that the impurity concentration exceeds the upper limit, it can be determined that due to some cause, there is a possibility that the remaining wafers may also contain the impurity at concentrations exceeding the reference value. In this case, it can also be determined that there is a possibility that the manufacture of the wafer, e.g., the formation of an epitaxial layer is out of specification.

Accordingly, when the above-mentioned sampling inspection is performed at a predetermined frequency, a possibility of shipping a wafer product whose impurity concentration exceeds the upper limit can be decreased. In addition, if a wafer product whose impurity concentration exceeds the upper limit is found, a possibility of manufacturing a large number of wafer products whose impurity concentrations exceed the upper limit can be decreased by investigating the cause of the increase in carbon concentration, or an out-of-specification state in the manufacturing process. As a consequence, the yield improves.

As described above, using this manufacturing method, the quality and manufacture of a wafer product can be managed. Note that if the result of the comparison of the carbon concentration with the upper limit indicates that the carbon concentration is equal to or lower than the upper limit, it may be determined that the wafer quality has no problem.

The semiconductor wafer manufactured by this manufacturing method is not limited to an epitaxial silicon wafer, and the impurity measured is not limited to carbon.

A practical example of the present invention will be described below.

Epitaxial layers were grown on 8-inch silicon wafers by using a lamp heating type epitaxial growth apparatus, thereby manufacturing epitaxial silicon wafers.

These silicon wafers were used as first samples, and carbon was ion-implanted into these samples such that the implantation dose was $5 \times 10^{10}$ to $5 \times 10^{14}$ ions/cm$^2$. After that, crystallinity recovery annealing was performed under a nitrogen atmosphere at a temperature of 900° C. This crystallinity recovery annealing was performed for 2 hrs in order to reliably recover the crystallinity of silicon.

Then, the wafers were irradiated with an electron beam at an acceleration energy of 4.6 MeV and an irradiation dose of $1 \times 10^{15}$ electrons/cm$^2$. This electron beam irradiation was performed while monitoring so that the wafer temperature did not exceed 60° C., and performing air cooling as needed.

After it was confirmed that unstable irradiation defects of each first sample stabilized, PL measurement was performed. More specifically, an excitation laser having a wavelength of 532 nm (penetration depth=2,500 nm) was used as the excitation light for PL measurement, and the sample surface intensity was set at 100 mW. In this PL measurement, each wafer was immersed in liquid helium, and spectral measurement was performed while the temperature was held at 4.2K, thereby obtaining the G-line intensity.

A graph shown in FIG. 1 was obtained by plotting the logarithm of the G-line intensity as a function of the logarithm of the ion implantation dose of carbon. This log-log plot of the G-line intensity with respect to the carbon implantation dose indicated a linear relationship, and the fitting coefficient of a fitted curve of the plot exceeded 0.99. The slope of the fitted curve was 0.76.

The G-line intensity of the epitaxial silicon wafer as the second sample was measured by the PL method. The second sample was a sample in which a large amount of carbon had been mixed into the epitaxial layer when it was formed. Electron beam irradiation, PL measurement, and the like were performed on the second sample under the same conditions as those for the epitaxial silicon wafer as the first sample. Then, the concentration of carbon contained in the wafer was obtained by SIMS measurement. Plot points obtained from these results were determined, and a line passing the points and having a slope of 0.76 as obtained above was drawn, thereby obtaining a calibration curve representing the relationship between the carbon concentration in the epitaxial silicon wafer and the G-line intensity, as shown as a graph in FIG. 2.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A formation method of forming a calibration curve, characterized by comprising:
   ion-implanting different doses of an impurity into a plurality of first samples made of the same semiconductor;
   measuring by a photoluminescence spectroscopy, for each of the plurality of first sample into which the impurity is ion-implanted, an intensity of photoluminescence deriving from the impurity, and obtaining a relationship between the dose of the implanted impurity and the intensity of the photoluminescence;
   measuring by the photoluminescence spectroscopy, for a second sample made of the same semiconductor as that of the plurality of first samples, an intensity of photoluminescence deriving from the impurity contained in the second sample, the measurement being performed under the same conditions as those for the measurement by the photoluminescence spectroscopy of the intensity of the photoluminescence for each of the plurality of first samples; and
   forming, based on the relationship, the intensity of the photoluminescence obtained for the second sample, and a concentration of the impurity contained in the second sample, which is measured by a method other than the photoluminescence spectroscopy, a calibration curve representing a relationship between the concentration of the impurity and the intensity of the photoluminescence deriving from the impurity.

2. The method according to claim 1, characterized in that the second sample is a sample in which the impurity has been introduced into a crystal made of the semiconductor during growth of the crystal, and contains the impurity at a concentration higher than that of each of the plurality of first samples into which the impurity is ion-implanted.

3. The method according to claim 1, characterized in that the method other than the photoluminescence spectroscopy is a method using secondary ion mass spectrometry.

4. The method according to claim 1, characterized by further comprising heating each of the plurality of first samples after the impurity is ion-implanted into the first sample, and before the photoluminescence deriving from the impurity ion-implanted into the first sample is measured.

5. The method according to claim 4, characterized in that a temperature of the heating is 700° C. to 1,200° C.

6. The method according to claim 1, characterized in that the semiconductor includes silicon, and the impurity is carbon.

7. The method according to claim 6, characterized in that each of the plurality of first samples and the second sample includes a silicon layer formed by epitaxial growth.

8. The method according to claim 6, characterized in that the photoluminescence deriving from the impurity implanted into the first sample and the photoluminescence deriving from the impurity contained in the second sample are G-line luminescence.

9. The method according to claim 1, characterized in that the amount of the impurity implanted into the plurality of first samples is $1\times10^9$ ions/cm$^2$ to $1\times10^{16}$ ions/cm$^2$.

10. The method according to claim 1, characterized in that the measuring by the photoluminescence spectroscopy for each of the plurality of first samples includes irradiating each of the plurality of first samples with an electron beam to render the impurity in the first sample luminescence-active, and the measuring by the photoluminescence spectroscopy for the second sample includes irradiating the second sample with an electron beam reder the impurity in the second sample luminescence-active.

11. The method according to claim 10, characterized in that an irradiation dose of the electron beam with which each of the plurality of first samples and the second sample is irradiated is $1\times10^{13}$ electrons/cm$^2$ to $1\times10^{17}$ electrons/cm$^2$.

12. A measurement method of measuring an impurity concentration in a semiconductor by using a calibration curve formed by a formation method according to claim 1, characterized by comprising:
   measuring by a photoluminescence spectroscopy, for a first measurement target made of a semiconductor manufactured under the same conditions as those for the first sample, an intensity of photoluminescence deriving from an impurity contained in the first measurement target; and
   obtaining a concentration of the impurity contained in the first measurement target by referring the intensity of the photoluminescence deriving from the impurity contained in the first measurement target to the calibration curve.

13. A manufacturing method of manufacturing a semiconductor wafer by using a measurement method according to claim 12, characterized by comprising:
   manufacturing a plurality of wafers made of a semiconductor;
   extracting a portion of the plurality of wafers, using at least a portion of the extracted wafers as a first measurement target, and measuring a concentration of an impurity contained in the extracted wafer by using the measurement method;
   comparing the concentration of the impurity contained in the extracted wafer with a predetermined upper limit; and
   if the concentration of the impurity contained in the extracted wafer exceeds the upper limit, determining that the rest of the plurality of wafers may also have a high impurity concentration, or determining that the manufacturing of the plurality of wafers is out of specification.

* * * * *